US012275680B2

United States Patent
Ren et al.

(10) Patent No.: US 12,275,680 B2
(45) Date of Patent: Apr. 15, 2025

(54) METHOD FOR PRODUCING 1,4-DIMETHYLTETRALIN

(71) Applicants: Sinochem Hebei Fuheng Co., LTD, Hebei (CN); Sato Planning Co., Ltd, Ibaraki (JP)

(72) Inventors: Jianpo Ren, Hebei (CN); Lieyi Ji, Hebei (CN); Junsheng Wang, Hebei (CN); Bingbing Zhang, Hebei (CN)

(73) Assignees: Sinochem Hebei Fuheng Co., LTD, Hebei (CN); Sato Planning Co., Ltd, Ibaraki (JP)

( * ) Notice: Subject to any disclaimer, the term of this patent is extended or adjusted under 35 U.S.C. 154(b) by 0 days.

(21) Appl. No.: 17/927,458

(22) PCT Filed: Aug. 10, 2021

(86) PCT No.: PCT/CN2021/111656
§ 371 (c)(1),
(2) Date: Nov. 23, 2022

(87) PCT Pub. No.: WO2022/257261
PCT Pub. Date: Dec. 15, 2022

(65) Prior Publication Data
US 2024/0228408 A1    Jul. 11, 2024

(30) Foreign Application Priority Data
Jun. 7, 2021 (CN) .......................... 202110633215.7

(51) Int. Cl.
*C07C 15/24* (2006.01)
*C07C 15/20* (2006.01)

(52) U.S. Cl.
CPC .......... *C07C 15/24* (2013.01); *C07C 2602/10* (2017.05)

(58) Field of Classification Search
None
See application file for complete search history.

(56) References Cited

U.S. PATENT DOCUMENTS

| | | | |
|---|---|---|---|
| 3,775,497 A * | 11/1973 | Thompson | C07C 15/24 585/479 |
| 3,840,609 A | 10/1974 | Oka et al. | |
| 3,843,737 A | 10/1974 | Chong | |
| 4,950,825 A | 8/1990 | Sikkenga et al. | |
| 4,962,260 A | 10/1990 | Sikkenga et al. | |
| 5,030,781 A | 7/1991 | Sikkenga et al. | |
| 5,034,561 A | 7/1991 | Sikkenga et al. | |
| 5,284,987 A | 2/1994 | Sikkenga et al. | |
| 5,401,892 A | 3/1995 | Sikkenga et al. | |
| 5,446,226 A | 8/1995 | Ozawa et al. | |
| 6,127,589 A | 10/2000 | Jakkula et al. | |
| 6,472,576 B1 | 10/2002 | Bergström et al. | |
| 7,935,856 B2 | 5/2011 | Soh et al. | |
| 2007/0232842 A1 | 10/2007 | Soh et al. | |

FOREIGN PATENT DOCUMENTS

| | | |
|---|---|---|
| CN | 101050161 A | 10/2007 |
| EP | 0612706 A1 | 8/1994 |
| EP | 0866045 A1 | 9/1998 |
| EP | 1031550 A1 | 8/2000 |
| GB | 1502170 A | 2/1978 |
| JP | S4875557 A | 10/1973 |
| JP | S49093348 A | 9/1974 |
| JP | S49-134634 A | 12/1974 |
| JP | S51101963 A | 9/1976 |
| JP | S5549053 B2 | 12/1980 |
| JP | H03500052 A | 1/1991 |
| JP | H04230226 A | 8/1992 |
| JP | H05213786 A | 8/1993 |
| JP | H05-255138 A | 10/1993 |
| JP | H07061941 A | 3/1995 |
| JP | 2000239194 A | 9/2000 |
| JP | 2007-277216 A | 10/2007 |
| KR | 20070099241 A | 10/2007 |

OTHER PUBLICATIONS

Office Action (Notice of Reasons for Refusal) issued Oct. 10, 2023, by the Japan Patent Office in corresponding Japanese Patent Application No. 2022-570585, and an English translation of the Office Action. (5 pages).
International Search Report issued in PCT/CN2021/111656, mailed Nov. 29, 2021, 5 pages (partial English translation).
Zhen, "Chemical Process Safety" NDRC Press, (Jun. 30, 2007), pp. 103, with English translation. (5 pages).
Office Action (The First Office Action) issued Nov. 18, 2024, by the State Intellectual Property Office of People's Republic of China in corresponding Chinese Patent Application No. 202110633215.7 and an English translation of the Office Action. (16 pages).

* cited by examiner

*Primary Examiner* — Tam M Nguyen
(74) *Attorney, Agent, or Firm* — Buchanan Ingersoll & Rooney PC

(57) ABSTRACT

By the control of the cyclization of 5-phenyl-2-hexene at a predetermined temperature, 1,4-dimethyltetralin is efficiently produced. The present invention provides a method for producing 1,4-dimethyltetralin, including a step of cyclizing 5-phenyl-2-hexene under reflux of solvents in the presence of acid catalysts.

4 Claims, No Drawings

METHOD FOR PRODUCING 1,4-DIMETHYLTETRALIN

CROSS REFERENCE TO RELATED APPLICATIONS

This application is the U.S. National Phase Application of International Application No. PCT/CN2021/111656, titled "METHOD FOR PRODUCING 1,4-DIMETHYLTETRALIN", filed on Aug. 10, 2021, which claims priority to Chinese Patent Application No. 202110633215.7, titled "METHOD FOR PRODUCING 1,4-DIMETHYLTETRALIN", filed on Jun. 7, 2021 with the China National Intellectual Property Administration, which is incorporated herein by reference in entirety.

FIELD OF THE INVENTION

The present invention relates to a method for producing 1,4-dimethyltetralin (sometimes abbreviated as 1,4-DMT) by cyclization of 5-phenyl-2-hexene (hereinafter sometimes abbreviated as PH).

BACKGROUND OF THE INVENTION

As shown in the following chemical formula, 1,4-DMT (2) is useful as a raw material of 1,4-dimethylnaphthalene (3) which is an intermediate material of 1,4-naphthalenedicarboxylic acid (4). It is known that 1,4-naphthalenedicarboxylic acid (4) has a wide range of application such as raw materials of dyes and resin.

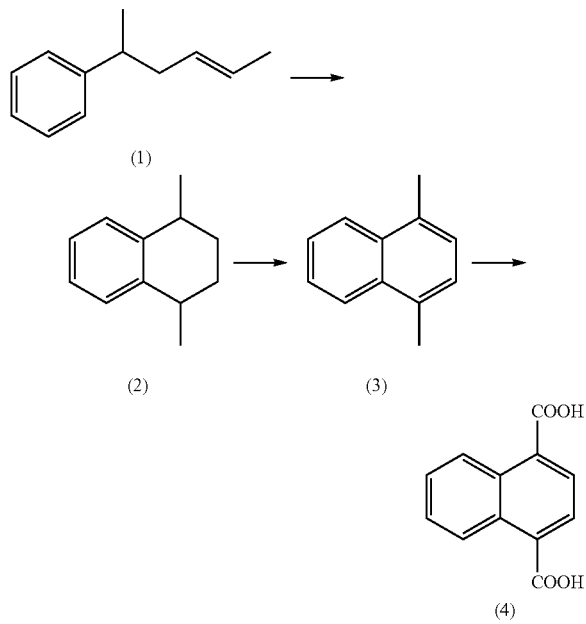

However, for the production of dimethyltetralins by cyclization reaction, as shown in the following chemical formula, it has been extensively studied to obtain 1,5-dimethyltetralin (6) (hereinafter, sometimes abbreviated as 1,5-DMT) on the basis of cyclization of 5-(o-tolyl)-2-pentene (5) (hereinafter, sometimes abbreviated as OTP). 1,5-DMT is useful as an intermediate for producing 2,6-naphthalenedicarboxylic acid (7).

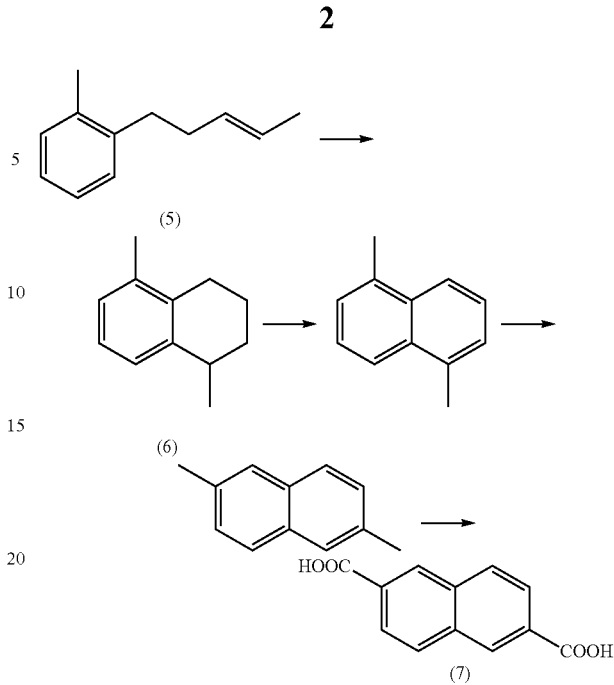

(5) (6) (7)

The following methods are disclosed for the cyclization of OTP. Patent Documents 1~5 disclose mainly using crystalline silica-alumina (e.g., Zeolite) as cyclization catalysts for OTP 5. As other catalysts, Patent Document 6 discloses the use of solid phosphoric acid or the like.

It is known that diluents are used in the above-mentioned cyclization reaction in order to suppress side reactions, and an example that solvents are used as the above-mentioned diluents is disclosed. In Patent Document 6, hexane, cyclohexane, octane, dimethyloctane, benzene, toluene, xylene, tetralin or dimethyltetralin, and other solvents are described as examples of diluents used as necessary in the reaction tower-like continuous cyclization reaction of OTP. However, the specific manner of using the above-mentioned diluents is not disclosed in embodiments or the like. Patent Document 7 discloses a method of performing cyclization reaction in the presence of aliphatic hydrocarbons in order to prevent side reactions.

Patent Document 1 discloses a method of using 10~60% of zeolite catalyst with respect to the reactants in the above-mentioned cyclization reaction and using o-xylene as a diluent. In addition, it is disclosed that problem of temperature control in the reaction is incurred since the cyclization reaction of OTP is a violent exothermic reaction (22 kcal/mol).

As for a measure against exothermic heat in the cyclization reaction of OTP (as a measure against exothermic heat in the cyclization reaction of OTP), a method is known in which the cyclization reaction of OTP is performed using fixed bed catalysts, and a part of the reaction product extracted from the reaction zone having the above-mentioned fixed bed catalysts is cyclized while circulated in a cooler provided outside (Patent Document 8, Patent Document 9). In addition, as another method, a method of refluxing while cyclizing OTP under reduced pressure using zeolite as a catalyst is known (Patent Document 10, Patent Document 11). As another example, Patent Document 5 discloses that a cyclization reaction is performed using zeolite and solvents that boil at 270° C. or higher. On the other hand, since the dehydrogenation reaction of 1,5-DMT is an endothermic reaction (about 30 Kcal/mol), it has been studied to simultaneously perform the above-mentioned cyclization reaction and dehydrogenation reaction in one step (Patent Document 12, Patent Document 13, Patent Reference 14). As described above, many research examples of the technology for producing 1,5-DMT based on the cyclization reaction of OTP are known.

However, as a method for efficiently removing the reaction heat of the cyclization reaction of OTP and controlling the reaction temperature, it is difficult to control the heat unevenness in the reaction tower by using a cooler outside the reaction tower. The method of utilizing the heat of evaporation of the reactant (OTP, boiling point of 227° C.) per se is to set a predetermined reaction temperature, and it is necessary to constantly adjust the degree of reduced pressure of the reaction system. In addition, 1,5-DMT (boiling point, 245~249° C.) is of a high concentration near the end point of the reaction, and it is difficult to proceed the reaction while controlling the temperature. In the method of simultaneously performing the cyclization reaction and the dehydrogenation reaction in one step, it is necessary to match the conditions of the cyclization reaction with the conditions of the dehydrogenation reaction, and there are problems such as easy occurrence of side reactions. On the other hand, the method of using solvents has only been studied as a mean of suppressing side reactions by dilution. In conclusion, it is difficult to proceed the cyclization reaction while controlling the temperature in the prior art.

On the opposite, little is known about the synthesis of 1,4-DMT by cyclization of PH. For example, a method of cyclizing PH at 100~450° C. using phosphoric acid and/or solid phosphoric acid as catalysts is known (Patent Document 15). Patent Document 5, Patent Document 10, or Patent Document 16 illustrates a method of cyclizing PH using zeolite (crystalline silica-alumina) as a catalyst. In addition, Patent Document 17 discloses a method for producing 1,4-dimethylnaphthalene (hereinafter, sometimes abbreviated as 1,4-DMN) via 1,4-DMT from PH by continuously performing gas-phase cyclization and gas-phase dehydrogenation in the presence of hydrogen. In this method, amorphous silica-alumina catalysts are used as the cyclization catalysts.

Similar to the cyclization reaction of OTP, since the cyclization reaction of PH is a severe exothermic reaction, a measure against this exothermic heat is required. However, the measure against the exothermic heat of the cyclization reaction of PH has not been sufficiently studied, and improvement is still required.

PRIOR ART DOCUMENT

Patent Document

Patent Document 1: Korean Patent Publication No. 20070099241
Patent Document 2: US Patent Publication No. 2007/0232842
Patent Document 3: U.S. Pat. No. 5,401,892
Patent Document 4: Japanese Patent H07061941
Patent Document 5: Japanese Patent H03500052
Patent Document 6: Japanese Patent S49093348
Patent Document 7: Japanese Patent 2000239194
Patent Document 8: Japanese Patent S51101963
Patent Document 9: U.S. Pat. No. 3,843,737
Patent Document 10: U.S. Pat. No. 5,284,987
Patent Document 11: Japanese Patent H04230226
Patent Document 12: U.S. Pat. No. 6,472,576
Patent Document 13: U.S. Pat. No. 6,127,589
Patent Document 14: Japanese Patent H05213786
Patent Document 15: Japanese Patent S4875557
Patent Document 16: U.S. Pat. No. 4,950,825
Patent Document 17: U.S. Pat. No. 3,775,497

SUMMARY OF THE INVENTION

The present invention has been made on the basis of such a situation. An object of the present invention is to provide a method for efficiently producing 1,4-DMT by controlling the cyclization of PH at a predetermined temperature.

The present inventors have conducted deep studies in order to solve the above-mentioned problems. As a result, it was found that by cyclizing PH in the presence of acid catalysts and under reflux of solvents, the reaction can be prevented from running out of control, and by carrying out the cyclization reaction while controlling the reaction temperature, 1,4-DMT can be produced in a good cyclization yield, so that the present invention was completed.

That is, the present invention includes the following aspects.

(1) A method for producing 1,4-dimethyltetralin, comprising the step of cyclizing 5-phenyl-2-hexene under reflux of solvents in the presence of acid catalysts.
(2) The method for producing 1,4-dimethyltetralin according to (1), wherein the acid catalysts are solid acid catalysts.
(3) The method for producing 1,4-dimethyltetralin according to (1) or (2), wherein the method comprises a step of producing 5-phenyl-2-hexene by the reaction of ethylbenzene with 1,3-butadiene, and excess ethylbenzene in the reaction liquid is used as the solvent.
(4) The method for producing 1,4-dimethyltetralin according to any one of (1)~(3), wherein the step of cyclization is performed in an intermittent method, a continuous method, or a semi-continuous method.

Invention Effect

According to the present invention, cyclizing PH under reflux of the solvent can prevent the reaction from running out of control, and the cyclization reaction can be performed while the reaction temperature is controlled. In addition, the cyclization yield can be improved by the control of reaction temperature.

DETAILED DESCRIPTION OF EMBODIMENTS

<5-phenyl-2-hexene (PH)>

PH as a raw material can be produced by any method, and can be produced by methods known per se. In addition, commercial products are also available. Geometric isomers based on the double bond at the 2-position of hexene exist in PH. In the present invention, it can be either a cis isomer or a trans isomer. The above-mentioned raw materials may contain 5-phenyl-1-hexene, which is a structural isomer of PH. With respect to the total mass of the above-mentioned raw materials, the content of PH is preferably 5% by mass or more, more preferably 100% by mass.

One aspect of the method for synthesizing PH(1) is, e.g. reacting ethylbenzene (8) with 1,3-butadiene (9) in the presence of basic catalysts such as metallic sodium and/or metallic potassium to obtain PH(1).

Another aspect of the synthesis method of PH (1) is, e.g. reacting excess ethylbenzene (8) with 1,3-butadiene (9) in the presence of basic catalysts such as metallic sodium and/or metallic potassium and then separating the above-mentioned catalysts to obtain PH in the form of ethylbenzene solution. A fraction containing PH of a high concentration can be obtained by the distillation of the ethylbenzene solution of this PH, and then can be used for the cyclization reaction. Herein, as a fraction containing PH of a high concentration, it is preferable to contain 5~100% by mass of PH, preferably 10~100% by mass of PH, more preferably 80~98% by mass of PH, and typically 95% by mass of PH with respect to the total mass of the above-mentioned fraction. Components other than PH of the above-mentioned fraction can mainly be ethylbenzene.

The above-mentioned distillation can be a known method per se, and can be vacuum distillation, atmospheric distillation, or pressurized distillation.

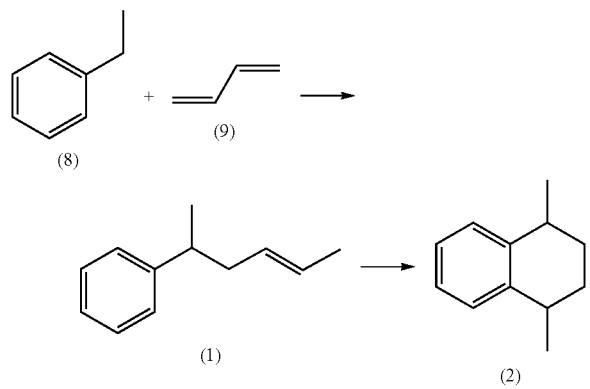

Although basic catalysts used for the reaction of ethylbenzene and 1,3-butadiene can be in a large amount, the post-treatment after the reaction can be troublesome. Therefore, the above-mentioned basic catalyst, e.g. metallic sodium, can be 0.005~0.7 mol, preferably 0.02~0.4 mol with respect to 1 mol of 1,3-butadiene.

In the reaction of ethylbenzene and 1,3-butadiene, they are stoichiometrically reacted in an equimolar amount, but in actual reaction, it is preferable that an excess of ethylbenzene is present. As one aspect of the present invention, 1.0~10 mols, preferably 1.1~8 mols of ethylbenzene can be used with respect to 1 mol of 1,3-butadiene.

The above reaction can be carried out in the absence or presence of solvents. As a solvent that can be used in the reaction, tetrahydrofuran and the like are preferable.

In addition, in this reaction, as cocatalysts, e.g. naphthalene, biphenyl, etc. can also be used. When such a cocatalyst is used, e.g. it can be used in an amount of 0.01~5 mol, preferably 0.05~2 mol with respect to 1 mol of metallic sodium and metallic potassium.

As another aspect of the present invention, in the reaction of ethylbenzene and 1,3-butadiene, when ethylbenzene is used in excess, ethylbenzene can be the solvent and reactant of the reaction. In this case, the usage-amount of ethylbenzene can be, e.g. 1.1~20 mol, preferably 1.2~10 mol with respect to 1 mol of 1,3-butadiene.

When ethylbenzene is used as a solvent and a reactant, it can be used in combination with other solvents. As another solvent, the following solvents are listed.

The reaction can be carried out under reduced pressure, normal pressure, or increased pressure, preferably under normal pressure or slightly increased pressure.

The reaction temperature of the reaction of ethylbenzene and 1,3-butadiene can be usually 50~150° C., more preferably 90~130° C. The reaction time is usually 30 minutes~72 hours, preferably 1 hour~36 hours.

The PH-containing reaction liquid obtained in the above-mentioned reaction can be post-treated by a method known per se, and PH can be separated and/or purified by a distillation method using a distillation column, or it can be used for the following cyclization reaction without separation and/or purification.

Production of 1,4-dimethyltetralin (1,4-DMT)

As one embodiment of the present invention, 1,4-dimethyltetralin (1,4-DMT) can be produced by the cyclization of 5-phenyl-2-hexene (PH) under reflux of solvents in the presence of acid catalysts.

Various acid catalysts can be exemplified as the acid catalysts used in the cyclization reaction of PH. For example, various acid catalysts known as isomerization catalysts per se can be used. In the cyclization reaction of PH, when the acidity of the acid catalysts is too high, side reactions are likely to occur, and when the acidity is too low, the reaction tends to be difficult to proceed. Therefore, when acid catalysts with a low acidity are used, it is necessary to carry out the reaction at a high reaction temperature. On the other hand, solid acid catalysts are preferable because of easy separation after the cyclization reaction.

As the acid catalysts used in the PH cyclization reaction according to one embodiment of the present invention, sulfuric acid, hydrogen chloride, phosphoric acid, hydrogen fluoride, sulfonic acids such as p-toluenesulfonic acid, and other solid acids such as silica-alumina, silica-magnesia, silica-calcia, etc. are listed. Among them, silica-alumina is preferable, and amorphous silica-alumina is more preferable.

The amount of the acid catalysts used for the cyclization reaction of PH can be, e.g. 0.02~10% by mass, preferably 0.1~5% by mass of amorphous silica-alumina with respect to PH.

The solvents used in the cyclization reaction of PH are preferably solvents that have lower boiling points than that of PH (about 210° C.) and do not adversely affect the cyclization reaction. Specifically, solvents having a boiling point of 80° C.~200° C., preferably about 100° ° C.~150° C. are preferable.

As above-mentioned solvents, e.g., aromatic hydrocarbons such as toluene, dimethylbenzenes, ethylbenzene, isopropylbenzene, propylbenzene, trimethylbenzenes, methylethylbenzenes, etc.; cycloaliphatic hydrocarbons, such as cyclohexane, ethylcyclohexane, dimethylcyclohexanes, trimethylcyclohexane, etc., can be used alone or in combination.

At least at the start of the reaction, the usage amount of the above-mentioned solvents can be 0.05~20 times, more preferably 0.2~5 times in terms of volume ratio with respect to PH.

As one embodiment of the present invention, the cyclization reaction of PH can be carried out under reflux in a reactor equipped with a reflux cooler in the presence of the above-mentioned acid catalysts, while extracting a part of the solvent used.

The reaction temperature of the cyclization reaction of PH varies depending on the acid catalysts used, and it can usually be in the range of 50° C.~250° C., preferably 50° ° C.~220° C., and more preferably 100° ° C.~200° C. The reaction temperature can be controlled by the selection of the optimal solvent according to the target reaction temperature.

The cyclization reaction of PH can be carried out under any condition of reduced pressure, normal pressure, or increased pressure, depending on the type of solvent used. Here, "normal pressure" typically means 1 atm, but is not limited to this. That is, in this specification, "normal pressure" means the pressure in the reaction system of open system without the operation for decompression or pressurization. As an embodiment of the present invention, the cyclization reaction of PH is preferably carried out under normal pressure in operation, and solvents effective under normal pressure are preferable.

One embodiment of the present invention is characterized in that a part or all of the exothermic heat in the cyclization reaction of PH is absorbed by the heat of evaporation of the solvent used, and the evaporated solvent is cooled with a reflux cooler and refluxed to the reaction system. Compared with the liquid-liquid heat exchange using the jacket of the reaction vessel, the reflux cooler is the heat exchange between the vapor and the liquid (cooling water), and the thermal transmittance is extremely high. Therefore, there is also the advantage that efficient cooling can be performed with relatively smaller equipment.

The boiling point of the reaction liquid in the cyclization reaction of PH (i.e., the reaction temperature of the above-mentioned cyclization reaction) is determined by the type and concentration (ratio) of the solvent in the reaction liquid. Therefore, the above-mentioned solvent is refluxed while a part of the solvent is extracted to reduce the solvent concentration in the reaction system, so that the reaction temperature can be increased. That is, the reaction temperature can be controlled by the adjustment of the extraction amount of the above-mentioned solvent in the reflux cooler.

As one embodiment of the present invention, the reactor for performing the cyclization reaction of PH may be a reaction tank with a jacket or a reaction tank with a cooler outside, other than the above-mentioned reflux cooler. In addition, these coolers may be used in combination with the removal of the reaction heat by the heat of evaporation.

As one embodiment of the present invention, the reaction time of the PH cyclization reaction varies depending on the catalysts used, and in the case of a liquid-phase reaction, it is usually 1 hour~78 hours, preferably 2 hours~48 hours.

After the cyclization reaction of PH is completed, the desired 1,4-DMT can be obtained by performing post-treatment known per se. As a post-treatment method, after the separation of the catalysts, methods such as distillation and crystallization can be used, and distillation is preferable.

As described above, when ethylbenzene and 1,3-butadiene are reacted to produce PH, an ethylbenzene solution of PH can be obtained. The ethylbenzene solution of PH can undergo cyclization reaction under reflux directly or after distillation to adjust the concentrations of ethylbenzene and PH, while a part of ethylbenzene is distilled off in a reactor equipped with a reflux cooler. As described above, the reaction temperature can be controlled by the adjustment of the ethylbenzene concentration through distillation of a part of the ethylbenzene.

As one embodiment of the present invention, the production of 1,4-DMT, particularly the cyclization step of PH, is performed by an intermittent method, a continuous method, or a semi-continuous method. As one embodiment of the present invention, the production of 1,4-DMT, particularly the cyclization step of PH, can be performed by a liquid-phase reaction.

In the case of the intermittent method, the solvents can be extracted from the reflux liquid while the reflux state is maintained. Meanwhile most of PH is initially cyclized in the low temperature region, and gradually the temperature of the reaction liquid is increased to complete the cyclization reaction. In the case of the continuous method, the solvent solution of PH and the acid catalysts for the cyclization reaction are continuously added into the reactor, and the solvent is refluxed while a part of the solvent is distilled off from the reflux cooler so that a predetermined reaction temperature is reached. That is, the solvent concentration in the reaction liquid corresponding to the target reaction temperature can be maintained by the continuous extraction of the reaction liquid while the adjustment of the distillation of the solvent. The continuous method can be performed in one step or two or more steps. The semi-continuous method can be a method of intermittently adding PH, solvents and/or acid catalysts for cyclization reaction into a reactor, and a method of intermittently extracting reaction liquid from the reactor. Furthermore, by combining these, the remaining of unreacted PH can be reduced.

EXAMPLES

Hereinafter, the present invention will be described in more detail by examples and comparative examples, but the present invention is not limited thereto. It should be noted that all compositions (%) are % by mass.

Example 1

5.75 kg of ethylbenzene and 25 g of metallic sodium as a catalyst were placed into a 10-liter reaction vessel, and 735 g of 1,3-butadiene was added at 110° C. over 10 hours with stirring.

After the addition was completed, water was added to remove the metallic sodium. This operation was repeated twice to obtain a total of 13 kg of reaction liquid having 20.4% by mass of PH of and 55.8% by mass of ethylbenzene with respect to the mass of the reaction liquid.

700 g of the above-mentioned reaction liquid and 3 g of an amorphous silica-alumina catalyst (SiO2 83%, Al2O3 13%) were put into a 1,000 ml-capacity flask equipped with a stirrer and a reflux cooler. With stirring, refluxing was continued while a part of a fraction (solvent) was extracted. The temperature of the reaction liquid was raised to 178° C. over 4 hours, and this temperature was maintained for 4 hours. After the reaction liquid was cooled, the catalyst was filtered out to obtain 302 g of a solution of 1,4-DMT having 0.5% by mass or less of unreacted PH. The composition is shown below.

Ethylbenzene: 41% by mass
1,4-DMT: 43% by mass (90% yield)

Example 2

The following experiments were carried out using the distillate having 30% of PH and 65% of ethylbenzene obtained by the distillation of the reaction liquid having 20.4% of PH in Example 1.

700 g of the above-mentioned distillate having 30% of PH and 7.0 g of p-toluenensulfonic acid was put into a 1,000 ml-capacity flask equipped with a stirrer and a reflux cooler. With stirring, refluxing was continued while a part of a fraction (solvent) was extracted. The temperature of the reaction liquid was raised to 160° C. over 4 hours, and this temperature was maintained for 3 hours.

After the reaction, the catalyst was filtered out to obtain 540 g of a solution of 1,4-DMT having 0.5% or less of unreacted PH. The composition is shown below.
Ethylbenzene: 57% by mass
1,4-DMT: 35% by mass (90% yield)

Example 3

The following experiment was performed using the distillate containing 35% by mass of PH and 60% by mass of ethylbenzene obtained by the distillation of the reaction liquid having 20.4% by mass of PH in Example 1. 700 g of the above-mentioned distillate having 35% by mass of PH and 3 g of the same silica-alumina catalyst as in Example 1 were put into a 1,000 ml-capacity flask equipped with a stirrer and a reflux cooler. With stirring, refluxing was continued while a part of a fraction (solvent) was extracted. The temperature of the reaction liquid was raised to 170° C. over 4 hours, and this temperature was maintained for 6 hours. After the reaction liquid was cooled, the catalyst was filtered off to obtain 516 g of a solution of 1,4-DMT having 0.5% by mass or less of unreacted PH. The composition is shown below.
Ethylbenzene: 47% by mass
1,4-DMT: 45% by mass (94% yield)

Example 4

The following experiments were performed using the distillate having 95% by mass of PH of and 1% by mass of ethylbenzene obtained by the distillation of the reaction liquid having 20.4% by mass of PH in Example 1.
350 g of the above-mentioned distillate, 400 g of ethylcyclohexane, and 4 g of the same silica-alumina as in Example 1 were put into a 1000 ml-capacity flask equipped with a stirrer and a reflux cooler. With stirring, refluxing was continued while a part of a fraction (solvent) was extracted. The temperature of the reaction liquid was raised to 170° C. over 4 hours, and this temperature was maintained for 6 hours. After the reaction liquid was cooled, the catalyst was filtered off to obtain 486 g of a solution of 1,4-DMT having 0.5% by mass or less of unreacted PH. The composition is shown below.
Ethylcyclohexane: 31% by mass
1,4-DMT: 65% by mass (94% yield)

Example 5

The continuous reaction was carried out using the distillate having 35% by mass of PH of and 60% by mass of ethylbenzene obtained in Example 3. The above-mentioned PH solution was continuously added at a rate of 200 g per hour, and the same silica-alumina catalyst as in Example 1 was continuously added at a rate of 2 g per hour into a 1000 ml-capacity flask with a stirrer and a reflux cooler. The reaction liquid was extracted from the flask to maintain the liquid level at 800 ml. The temperature of the reaction liquid was maintained at 180° C. while ethylbenzene and the like were distilled off from the reflux cooler. The amount of distillate such as ethylbenzene from the reflux cooler was 69 g per hour, and the flow rate of the reaction liquid was 133 g per hour. The reaction liquid after 24 hours was analyzed by gas chromatography. As a result, the composition of the reaction liquid was as follows.
Ethylbenzene: 39% by mass
1,4-DMT: 49% by mass (92% yield)
PH: 3%

Comparative Example 350 g of 95% by mass of PH of Example 4 and 3 g of the same silica-alumina as in Example 1 were added to a 1000-ml flask equipped with a stirrer, and reacted. The reaction temperature was gradually increased from normal temperature. As a result, an uncontrollable and abrupt temperature increase started from around 130° C., and the final temperature reached 210° C. After the reaction liquid was maintained at this temperature for 4 hours, it was cooled. The reaction liquid was analyzed by gas chromatography. As a result, the composition of the reaction liquid (343 g) was as follows.
1,4-DMT: 86% by mass (88% yield)
PH: 0.5% by mass or less

INDUSTRIAL AVAILABILITY

According to the present invention, by cyclizing PH under reflux of the solvent, it is possible to prevent the reaction from running out of control and to promote the cyclization reaction while controlling the reaction temperature. In addition, the cyclization yield can be improved by the control of the reaction temperature.

The above are only the preferable embodiments of the present invention. It should be noted that for those of ordinary skill in the art, without departing from the principles of the present invention, several improvements and modifications can be made. These improvements and modifications should also be regarded as the protection scope of the present invention.

The invention claimed is:
1. A method for producing 1,4-dimethyltetralin, comprising a step of cyclizing 5-phenyl-2-hexene under reflux of solvents in the presence of acid catalysts, wherein a reaction temperature is controlled in the step of cyclization by adjustment of an extraction amount of solvent in a reflux cooler.
2. The method for producing 1,4-dimethyltetralin according to claim 1, wherein the acid catalysts are solid acid catalysts.
3. The method for producing 1,4-dimethyltetralin according to claim 1, wherein the method comprises a step of producing 5-phenyl-2-hexene by the reaction of ethylbenzene with 1,3-butadiene, and excess ethylbenzene in the reaction liquid is used as the solvent.
4. The method for producing 1,4-dimethyltetralin according to claim 1, wherein the step of cyclization is performed in an intermittent method, a continuous method or a semi-continuous method.

* * * * *